(12) United States Patent
Lolacono et al.

(10) Patent No.: US 7,657,127 B2
(45) Date of Patent: Feb. 2, 2010

(54) METHOD AND APPARATUS FOR PROVIDING STROBED IMAGE CAPTURE

(75) Inventors: Dominick Lolacono, Yardville, NJ (US); James R. Matey, Princeton, NJ (US); Oleg Naroditsky, Princeton, NJ (US); Michael Tinker, Yardley, NJ (US); Thomas Zappia, Plainsboro, NJ (US)

(73) Assignee: Sarnoff Corporation, Princeton, NJ (US)

( * ) Notice: Subject to any disclaimer, the term of this patent is extended or adjusted under 35 U.S.C. 154(b) by 0 days.

(21) Appl. No.: 12/429,695

(22) Filed: Apr. 24, 2009

(65) Prior Publication Data

US 2009/0232418 A1 Sep. 17, 2009

Related U.S. Application Data

(63) Continuation of application No. 11/334,968, filed on Jan. 19, 2006, now Pat. No. 7,542,628.

(60) Provisional application No. 60/670,203, filed on Apr. 11, 2005.

(51) Int. Cl.
*G06K 9/00* (2006.01)

(52) U.S. Cl. .................................................. 382/312
(58) Field of Classification Search ................. 382/312, 382/313, 318, 321, 118; 378/108, 116; 351/221
See application file for complete search history.

(56) References Cited

U.S. PATENT DOCUMENTS

| 5,861,940 | A  | * | 1/1999  | Robinson et al. ............ 351/221 |
| 6,977,989 | B2 | * | 12/2005 | Bothe et al. ................. 378/108 |
| 7,095,901 | B2 |   | 8/2006  | Lee et al. |
| 7,466,847 | B2 | * | 12/2008 | Komura ....................... 382/118 |

FOREIGN PATENT DOCUMENTS

| EP | 1324259   | 7/2003 |
| WO | 199721188 | 6/1997 |
| WO | 199808439 | 3/1998 |
| WO | 200039760 | 7/2000 |

* cited by examiner

*Primary Examiner*—Anh Hong Do
(74) *Attorney, Agent, or Firm*—Lowenstein Sandler PC

(57) ABSTRACT

A method and apparatus for strobed image capture includes stroboscopic illumination synchronized with one or more cameras to improve a signal to noise ratio, reduce motion blur and avoid object damage in sensor systems used to analyze illumination sensitive objects.

31 Claims, 4 Drawing Sheets

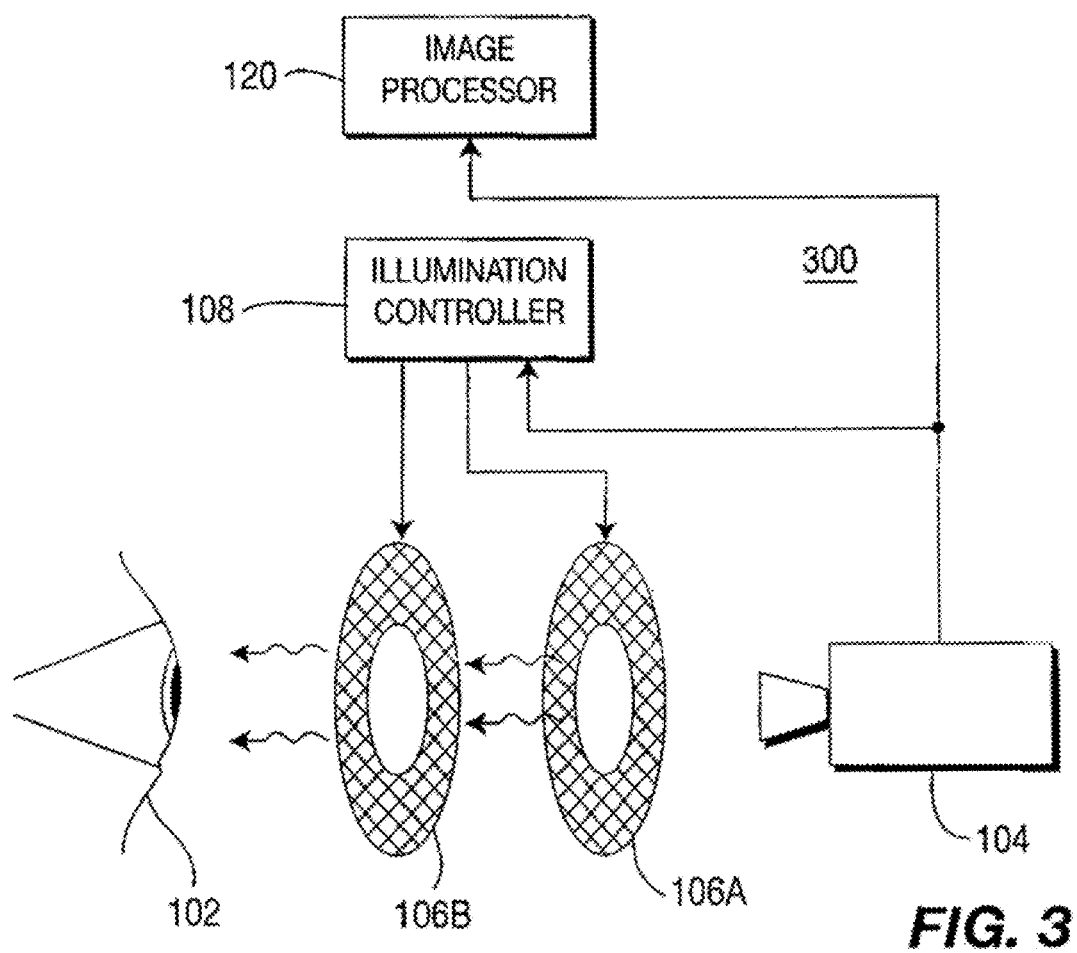
FIG. 3
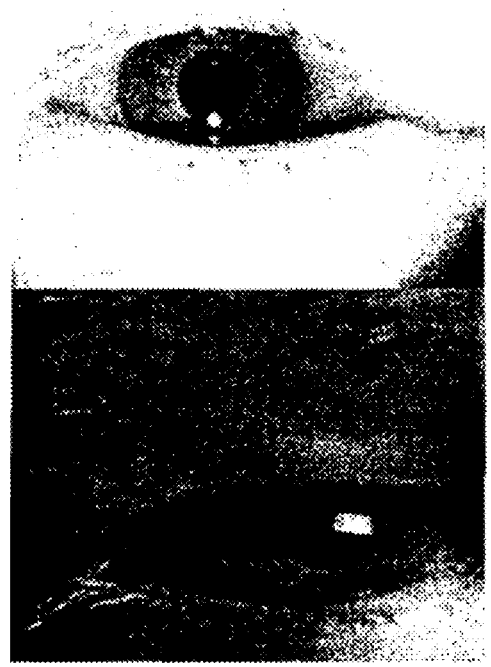
FIG. 4A
FIG. 4B

METHOD AND APPARATUS FOR PROVIDING STROBED IMAGE CAPTURE

CROSS-REFERENCE TO RELATED APPLICATIONS

This application claims is a continuation of co-pending U.S. application Ser. No. 11/334,968 filed Jan. 19, 2006, which claims the benefit of U.S. Provisional Application No. 60/670,203 filed on Apr. 11, 2005, which are herein incorporated by reference. In addition, this application is related to co-pending U.S. application Ser. No. 11/364/300 filed Feb. 28, 2006, which is incorporated by reference herein.

GOVERNMENT RIGHTS IN THIS INVENTION

This invention was made with U.S. government support under contract number NMA401-02-9-2001-0041. The U.S. government has certain rights in this invention.

BACKGROUND OF THE INVENTION

1. Field of the Invention

The invention relates generally to image capture for use in object sensor systems where the object is illumination sensitive. More specifically, one embodiment of the invention relates to strobed video capture for providing video images for use in biometric sensor systems.

2. Description of the Related Art

Imaging systems used in object monitoring or inspection are designed to generate accurate images of objects using a camera and sufficient illumination. In some instances, sufficient illumination to produce a useful image may be enough illumination to cause damage to, or otherwise alter, the object being imaged. One such object that can be damaged by excessive illumination is the human eye.

Biometric sensing techniques, where the human eye is monitored, have become useful in person identification and behavioral analysis. For example, iris recognition is a well known technique for identification, while pupillometry, the measure of a pupil's reaction to external stimuli, can be used for behavior analysis, e.g., detection of sleep deprivation, drug or alcohol abuse, and the like. To facilitate accurate biometric sensing using either iris recognition or pupillometry, images of the human eye must be accurately and clearly captured for analysis.

Commercial off-the-shelf video cameras typically run with a frame period of 33 ms, corresponding to a frame rate of 30 Hz. Often, eye movement occurs on that time scale. To avoid motion blur in images of the eye, the exposure time of each frame may be reduced using the electronic shutter capability found in many cameras. However, a reduction often times in shutter speed also reduces the signal-to-noise ratio (S/N) by ten times, all other parameters being held constant. If there are no restrictions on the irradiance of an object, the reduction in S/N and can be compensated for by increasing the scene irradiance (W/m$^2$). However, when imaging an eye there are strict restrictions on irradiance for safety considerations.

Therefore, there is a need in the art for a method and apparatus for irradiating a scene to enable an imaging system to capture accurate images of an object, such as an eye, without damaging the object.

SUMMARY OF THE DISCLOSURE

The invention is a method and apparatus for providing strobed image capture of an illumination sensitive object, for example, images of a subject's eye for biometric applications. The system may be used in any situation where an object that is being imaged is susceptible to damage from the radiation used to illuminate the object. In one embodiment of the invention, at least one strobed illumination source is controlled and at least one camera is synchronized with the strobed illumination source. The camera captures images (e.g. video) of the object. The object is illuminated at least in part by photons from the strobed illumination source while the camera captures images of the object, e.g., the iris and/or pupil of the eye. In one embodiment, the captured images of a subject's eye may be used for iris recognition or pupillometry. In a first embodiment of the invention, the images are processed to extract unique information regarding the iris for identification purposes. In a second embodiment, the strobed illumination source is used to stimulate a pupil reaction and the reaction is captured using the video camera. The pupil's reaction to the stimuli is analyzed to provide behavioral information about the subject. In a third embodiment, the saccadic motion of the pupil can be analyzed to provide behavioral information about the subject.

BRIEF DESCRIPTION OF THE DRAWINGS

The teachings of the present invention can be readily understood by considering the following detailed description in conjunction with the accompanying drawings, in which:

FIG. 3 depicts a block diagram of an embodiment of the invention for performing pupillometry:

FIGS. 4A and 4B illustrate the difference between a strobed image of eye during saccadic motion (4A) and an image using conventional lighting (4B):

To facilitate understanding, identical reference numerals have been used, where possible, to designate identical elements that are common to the figures.

DETAILED DESCRIPTION

The invention will be primarily described within the general context of a method and apparatus for providing video capture of iris images with strobed illumination synchronized to a video capture system. However, the invention may be used to control illumination of any object that is susceptible to damage from excessive illumination.

One exemplar) embodiment of the present invention is an illumination controller for light-emitting diode (LED)/laser diode arrays that can generate strobed illumination that is synchronized with a video camera. The duration, intensity and position of the illumination sources (strobes) with respect to the start of video frames are adjustable to optimize performance for specific applications. The light intensity is increased during the strobe period so that adequate S/N may be maintained, while the average irradiance remains below threshold limit values for safe exposure of the object. The need for this capability arises from work in biometrics of the human eye: (a) iris recognition and (b) pupillometry and saccadic motion analysis for investigations of fitness for duty.

Iris recognition is a well-known technique for identification. Pupillometry is the measurement of the pupil's response to external stimuli and may refer to autonomic constriction/dilation responses to light level. Saccadic motion is eye movement in which the eyes jump from one point to another. Pupil responses and saccadic motions are both influenced by drugs, alcohol and sleep deprivation. Such measurements could be used to screen operators of potentially dangerous equipment in real time, thereby reducing or eliminating the need to conduct more intrusive tests.

Figure 1:
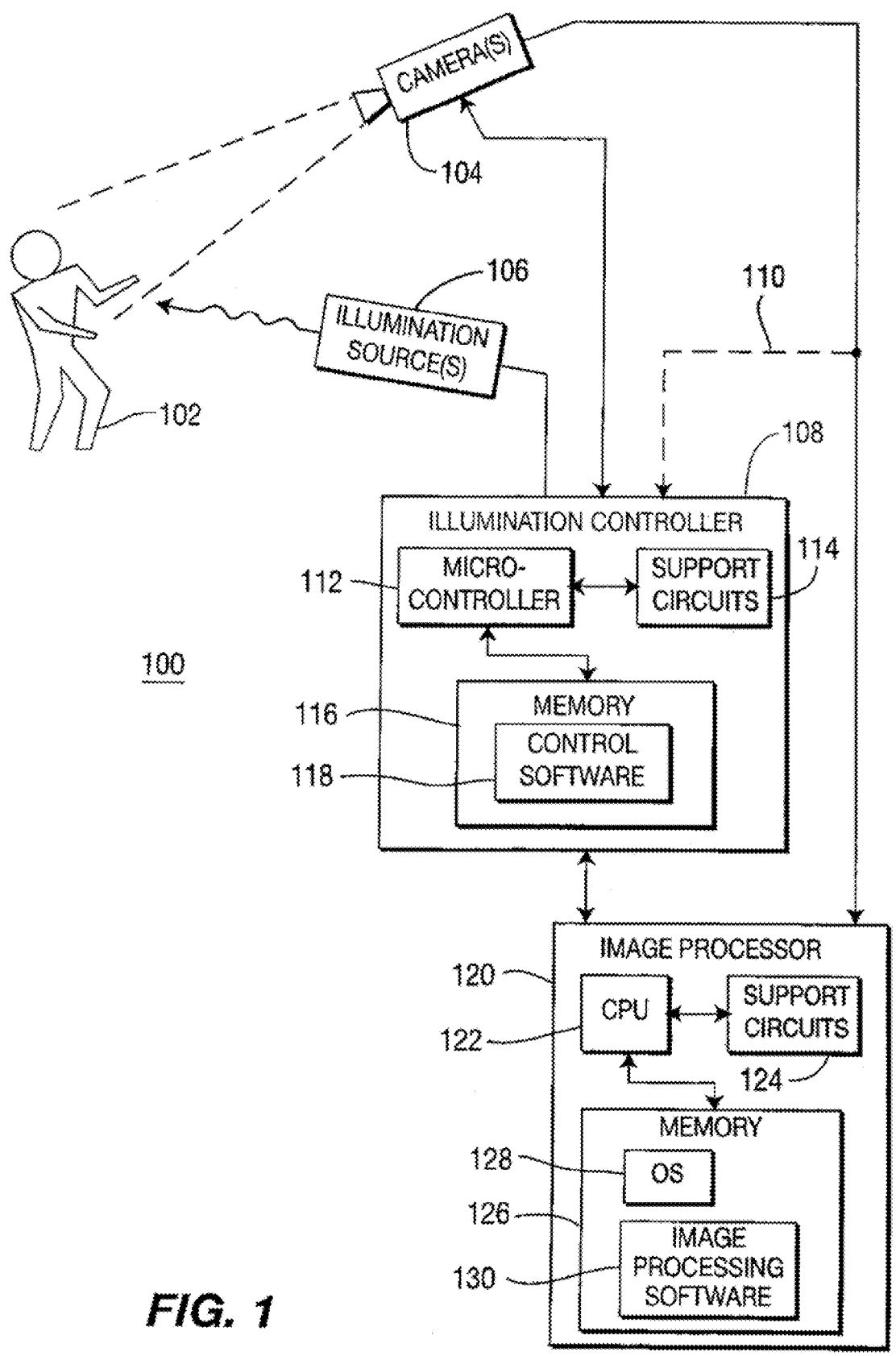
FIG. 1 is a block diagram illustrating an exemplary embodiment of an apparatus for strobed video capture, according to the present invention.

FIG. 1 shows an exemplary embodiment of an apparatus 100 for strobed video capture, according to the present invention. The apparatus 100 includes at least one camera 104, and at least one illumination source 106, an illumination controller 108 and an image processor 120. As discussed below, the illumination controller 108 and the image processor 120 may be combined into a single sub-system. In operation, the illumination controller 108 provides synchronization to or accepts synchronization from the camera 104. The illumination controller 108 generates control signals for the illumination source 106 that are synchronized to the camera 104. The illumination source 106 irradiates an object, for example, subject 102 and photons reflected from the subject 102 are captured by the camera 104. The subject 102 may be positioned near the camera/source combination or may be positioned at a large stand-off distance from the camera/source combination.

Either the camera 104 or the illumination controller 108 may be a source of timing signals, i.e., a timekeeper. The camera 104 may provide synchronization signals to the controller 108 or the controller 108 may provide synchronization to the camera 104. A variety of cameras 104 may be used. Some standard, analog cameras 104, such as RS-170 (EIA-170, Electronics Industry Alliance, Arlington. VA), have no provision for input of an external synchronization signal. For these cameras 104, the illumination controller 108 must accept the RS-170 signal as an input and derive synchronization signals from that signal. Other cameras 104, particularly digital cameras 104 using a camera link interface, can accept a trigger signal either directly or through a digital frame grabber card in a computer that is controlling the system. The desire to have a system able to handle a variety of cameras 104 led to the use of a microcontroller-based illumination controller 108.

The illumination controller 108 comprises a microcontroller 112, support circuits 114 and memory 116. The microcontroller may be any one of the many microcontrollers available including, for example, a ZWorld RCM 2100. The support circuits 114 comprise well known support circuits such as power supplies, clock circuits, registers, buffers, and the like. In addition, the support circuits may contain circuits for facilitating conversion of video signals into synchronization signals such as sync strippers, signal buffers, frame grabbers, and the like. In one embodiment, a video signal is provided on path 100 to enable the controller 108 to produce synchronization signals directly from the video images. The memory 116 may comprise random access memory, read only memory or any combination thereof. The memory 116 stores instruction (control software 118) for the microcontroller that facilitates creation of the synchronization signals.

The image processor 120 is coupled to the video camera 104 as the illumination controller 108. The image processor 120 comprises at least one central processing unit (CPU) 122, support circuits 124 and memory 126. The CPU 122 may be one of the many microprocessors that are commercially available. The support circuits 124 comprise well known circuits such as power supplies, clock circuits, cache, input/output circuits and the like. The memory 126 may comprise random access memory, read only memory, disk drives, removable memory, optical memory, network storage or any combination thereof. The memory 126 stores an operating system 128 and image processing software 130. The image processor may be a general-purpose personal computer or server that, when executing the image processing software, operates as an image processor to analyze the images captured of the subject's eye. The image processing software 130 may analyze the imagery using iris recognition techniques, pupillometry techniques, saccade motion analysis techniques and others.

Although the illumination controller 108 is depicted separately from the image processor 120, in another embodiment of the invention, the CPU 122 of the image processor 120 may perform the functions of the illumination controller microcontroller 112. Alternatively, the illumination controller may be a circuit card within the image processor 120.

Figure 2:
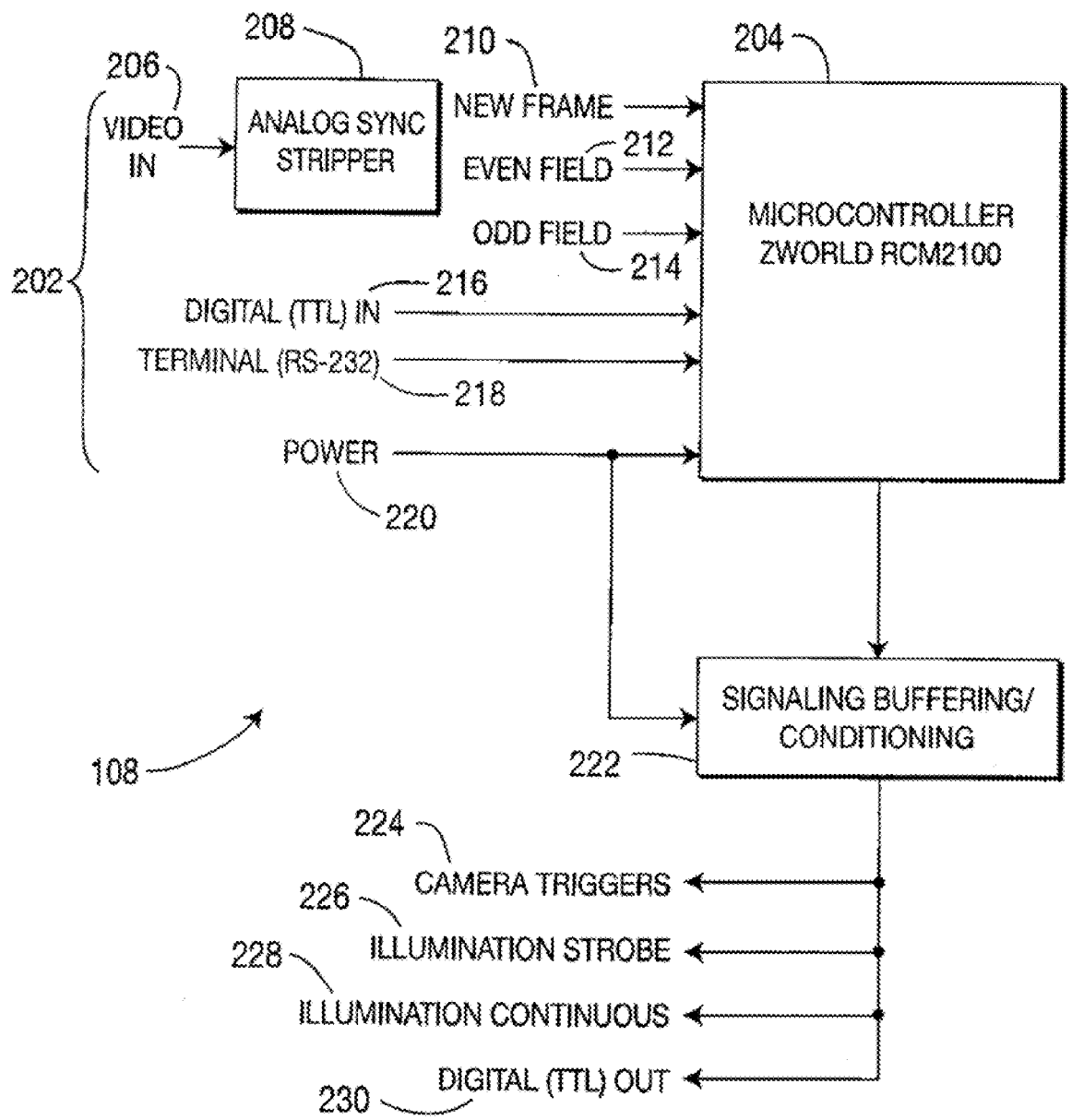
FIG. 2 depicts a block diagram of an illumination controller used in one embodiment of the invention.

FIG. 2 shows an exemplary embodiment of an illumination controller 108, according to the present invention. The inputs 202 to a microcontroller 204 are in the upper left of the diagram of FIG. 2. When available, analog video 206 from the camera 104 can be processed by an analog synch stripper chip 208 to generate digital signals corresponding to a new frame 210, an even field 212, and an odd field 214. These are input to the microcontroller 204 along with additional digital signals 216 that can vary from application to application. One example of an additional digital signal is a top of frame trigger from a digital camera. In this example, there is a provision for input of operational parameters to the microcontroller 204 via an RS-232 port 218. e.g. time delay of a strobe relative to start of frame.

A power input 220 is coupled to both the microcontroller 204 and the buffering and conditioning electronics 222. The buffering and conditioning electronics 222 takes the transistor-transistor logic (TTL) levels output by the microcontroller 204 and converts them to the levels appropriate for the cameras 104 and illumination source 106. In this example, triggers and strobes are buffered with one-shots that generate trigger pulses and strobes with pulse widths that are adjustable via onboard trim pots. The triggers and strobes also have adjustable analog delays. In one embodiment, the trigger and strobe widths may be set in analog hardware to reduce the load on the microcontroller 204 and simplify the microcontroller code. The strobe outputs are implemented as open collector, high power field effect transistors (FETs) that switch power from an external source to the illumination source 106. In an embodiment for performing pupillometry, two illumination sources are used—one continuous source and one strobed source. The continuous illumination outputs use the same type of FET output; however, in this case, the microcontroller enables an oscillator whose frequency and pulse width are set via onboard trim pots. In this example, the illumination controller 108 provides outputs including camera triggers 224, illumination strobe 226, illumination continuous 228, and digital (TTL) out 230, which are described in Table 1. The example circuit controls two light sources (white and IR) for use in pupillometry. The white source is a continuous source and the IR source can be either strobed or continuous under program control.

TABLE 1

Outputs Available from the Illumination Controller 108

| Camera triggers | Trigger pulse width set in analog hardware<br>Nominal pulse position set in analog hardware<br>Pulse position adjustable relative to video synch under program control |
| --- | --- |

TABLE 1-continued

Outputs Available from the Illumination Controller 108

| | |
|---|---|
| Illumination strobes | Switches external power supply |
| | Strobe width set in analog hardware |
| | Nominal strobe position set in analog hardware |
| | Strobe position adjustable relative to video synch under program control |
| Illumination continuous | Switches external power supply |
| | Pulse width modulation |
| | Enabled under program control |
| Digital TTL outputs | Direct from microcontroller |

Table 2 shows pseudo code for an exemplary application of the illumination controller 108. The controller 108 is first initialized and then there is a loop. At the top of the loop, the controller 108 waits for a signal from the synch stripper that indicates that a new frame is starting. Then, a frame grabber (not shown) is triggered. The controller 108 waits an appropriate time and, then triggers the light source 106. The frame that is currently being generated by the camera will see the effect of the strobed light source and the frame grabber will capture the frame.

TABLE 2

Exemplary pseudo code for a simple application

```
initializeIOSystem( );
for (;;) {
  waitOnVideoSynch( );
  triggerFrameGrabber( );
  delayMilliSeconds(delayTime);
  triggerStrobe( );
}
```

This high level description omits a number of timing details that are specific to the camera and frame grabber. Exemplary embodiments of the present invention can be designed to include those timing details by reviewing particular camera and frame grabber specifications and by constructing a timing diagram. An advantage to the microcontroller approach shown in FIG. 2 is that not only can the delay times under program control be varied, but it is also easy to switch between the two cases using directives to the microcontroller via the RS-232 port. As an example of a complication, consider that some frame grabbers may not capture the current frame when triggered, but may wait to start grabbing on the next frame. In this case the pseudo code in Table 3 would be more appropriate.

TABLE 3

Exemplary pseudo code for a slightly more complicated application

```
initializeIOSystem( );
waitOnVideoSynch( );
for (;;) {
  triggerFrameGrabber( );
  waitOnVideoSynch( );
  delayMilliSeconds(delayTime);
  triggerStrobe( );
}
```

Table 3 illustrates pseudo code for a real-time application. If the loop does not execute in less time than a frame time, synchronization between the strobe and the captured frames can be lost. In one embodiment, a microcontroller with low overhead and real time capability is used to operate the illumination controller.

Exemplary embodiments of the present invention have many applications. One application is saccadic motion analysis. Saccadic motion occurs when the eye abruptly changes its region of interest. Saccadic motion is not quite a reflex. The motion can be consciously initiated, but once started, the motion is effectively under the control of an uninterruptible low level subroutine in the nervous system; it becomes essentially involuntary. As an experiment, the reader can fix their gaze on an object at the left of their visual field of view and then abruptly shift the fixation point to an object on the right side and then shift it back. After several repetitions, try to halt the motion after initiation-halting the motion is essentially impossible, because it is under low level neural control. Another application is pupillometry. Pupillometry is the measurement of the reaction of the pupil to light stimuli. Although some people have some degree of control over the dilation of their pupils, this is also an essentially involuntary response. It is easy to see this effect. Under subdued lighting, look into a mirror and note the pupil diameter, then turn on a bright light while watching the pupil and after about 10 seconds turn the light off while continuing to watch the pupil.

Analysis of saccadic motions and pupil response provide data about the state of the nervous system and can enable the inference as to whether the nervous system has been degraded by drugs (legal or not), disease, alcohol and general physiological conditions including fatigue. Such analysis is interesting for determining fitness for duty in challenging or potentially dangerous occupations; it is a measure of the subject's reflexes.

FIG. 3 illustrates an exemplary apparatus 300 for analyzing saccadic motion and/or for performing pupillometry. In the depicted embodiment, the subject is near the camera/source combination such that a subject 102 peers at the camera 104 through the center of two illuminators 106A and 106B both of which are powered via one of the illumination controllers 108. The illuminators 106A and 106B are annular arrays of light emitting diodes. The camera 104 is focused through the annulus onto the eye of the subject 102. In one embodiment, the illuminator 106B nearer to the subject 102 can provide flashes of white light over a large field of view for pupillometry or can flash point source stimuli at the edges of the visual field as fixation points for saccadic motion. The illuminator 106A closer to the camera provides synchronized strobes in the near infra-red (IR) and the camera is filtered to reject visible light; hence the contrast and brightness of the images are unaffected by the visible light stimuli.

FIGS. 4A and 4B illustrate the difference between a strobed image of an eye during saccadic motion (4A) and an image using conventional lighting (4B). Compare the quality of the image acquired using strobed illumination (FIG. 4A) with the conventional image (FIG. 4B). In both images, eyelash details are clearly visible, the images are in focus, and both images provide good resolution. In the conventional image (FIG. 4B), the edges of the pupil are badly blurred (e.g., approximately 10 pixels). In the strobed image (FIG. 4A), they are sharp enough to enable measurement of the position and radius of the pupil (e.g. to within approximately 1 pixel). In the case of FIG. 4A, the strobe was about 6 ms duration roughly 20% of the frame time, which is consistent with the blur reduction that is seen.

The captured images are coupled from the camera 104 to the image processor 120. The image processor 120 executes image processor software (130 in FIG. 1) to process the images and analyze the pupil motion and/or response to the stimuli. Utilizing the present invention to capture sharp pupil images enables pupil motion and/or response analysis techniques to operate with greater accuracy.

In another application for the strobed image capture of the present invention shown in FIG. 1, a subject 102 is at a standoff distance from the camera 104 and illumination source 106 and the image processor 120 processes images of the subject's eye(s) to perform biometric iris recognition. The illumination controller 108 is used to optimize the amount of illumination exposure of the subject 102.

Iris recognition is one of the most reliable biometric identification technologies available. Most current iris recognition systems rely on algorithms developed by John Daugman of Cambridge University. These algorithms analyze images of the iris using wavelet decomposition to generate an iris code, a binary string that is unique to an individual iris. Codes from two iris images are compared by measuring the Hamming distance (the number of non-corresponding bits) between the two codes: a low Hamming distance is interpreted as a match. A commercially available version of the Daugman algorithms from Iridian, Inc. may be used.

Most commercial iris recognition systems require the subject to be positioned within a spatial capture volume for a defined length of time in order for the camera in the recognition system to acquire an iris image of sufficiently high quality that an iris code can be correctly generated. Current commercial systems assume that subjects are sufficiently cooperative that they will position themselves within the capture volume and remain there during the image capture process A capture volume for a typical commercial system is 1.5 cm×1.5 cm×10 cm. or a little over 20 cm$^3$ and requires that the subject remain still within that capture volume. By contrast, exemplary embodiments of the present invention enable capture of iris images of moving subjects in much large capture volumes.

Expansion of the capture volume can be achieved by increasing the number of pixels in the camera, by increasing the number of cameras, by increasing the depth of field or by doing all three. Multiple high-resolution cameras may be used to expand the capture volume to roughly 30 cm×60 cm×10 cm, or 18,000 cm$^3$. However, pixels are not useful if they are badly blurred. As previously discussed, saccadic motions can give blur of the order of approximately 10 pixels in an image with approximately 200 pixels across the iris in conventional images. Side-to-side motions induced by normal walking can give rise to blur of similar magnitude.

Blur could be reduced by reducing the shutter time of the camera, at the expense of efficiency in collecting photons. A ten times reduction in blur entails a ten times reduction in the number of photons collected by the camera sensor. In order to maintain the S/N, the number of photons incident on the subject needs to be increased by ten times. This may be accomplished by increasing the product of the number of illuminators times the intensity of their illumination by ten times. This approach presents a number of practical difficulties: illuminators are typically running at maximum continuous wave (CW) output already; increasing the number of illuminators by ten times increases the footprint of the system substantially; and increasing the irradiance at the subject by ten times can push a threshold limit value (TLV®) safety limits in some cases. TLVs are published by the American Conference of Governmental Industrial Hygienists (ACGIH®). In a more general case, for objects other than an iris, the TLV would be replaced by some appropriate measure of the object's sensitivity to photon damage.

By strobing the light sources, relief may be provided on two of these issues: the peak power output of the illuminators may be increased beyond the CW limits; the TLV® for peak power in a train of short pulses is higher than the CW limit. By combining strobed light sources with shuttering of the camera around the strobes, an additional advantage may be gained: reduction in the effects of ambient illumination. For a 10% duty cycle, ambient light is effectively reduced by ten times. If the controlled illumination can be increased during the strobe by a full ten times over the CW value, a full ten times improvement of S/N would be gained for noise related to ambient light. In practice the duty cycle of the illuminators cannot simply be reduced by a factor, X, and the output of the illuminators cannot be increased by the same factor to maintain a constant integrated light flux. This effect is shown in FIG. 5.

Figure 5:
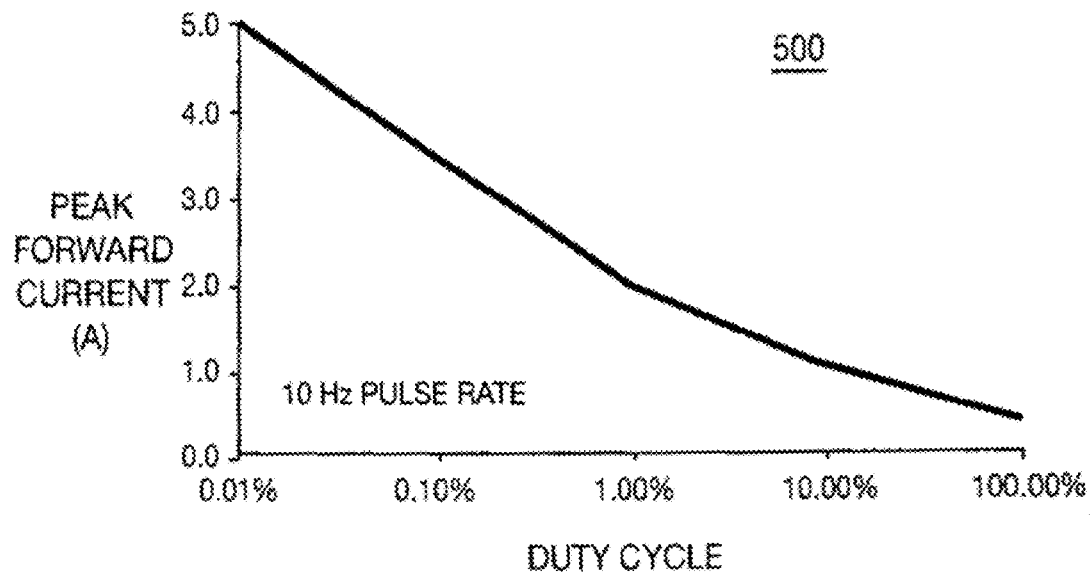
FIG. 5 is a chart illustrating a maximum allowable peak forward current as a function of duty cycle for a typical LED array at a 10 Hz pulse rate.

FIG. 5 is a chart 500 illustrating a maximum allowable peak forward current as a function of duty cycle for a typical LED array at a 10 Hz pulse rate. As shown in FIG. 5, a 1% duty cycle does result in a maximum allowable forward peak current that is ~100 times larger than the continuous case.

Figure 6:
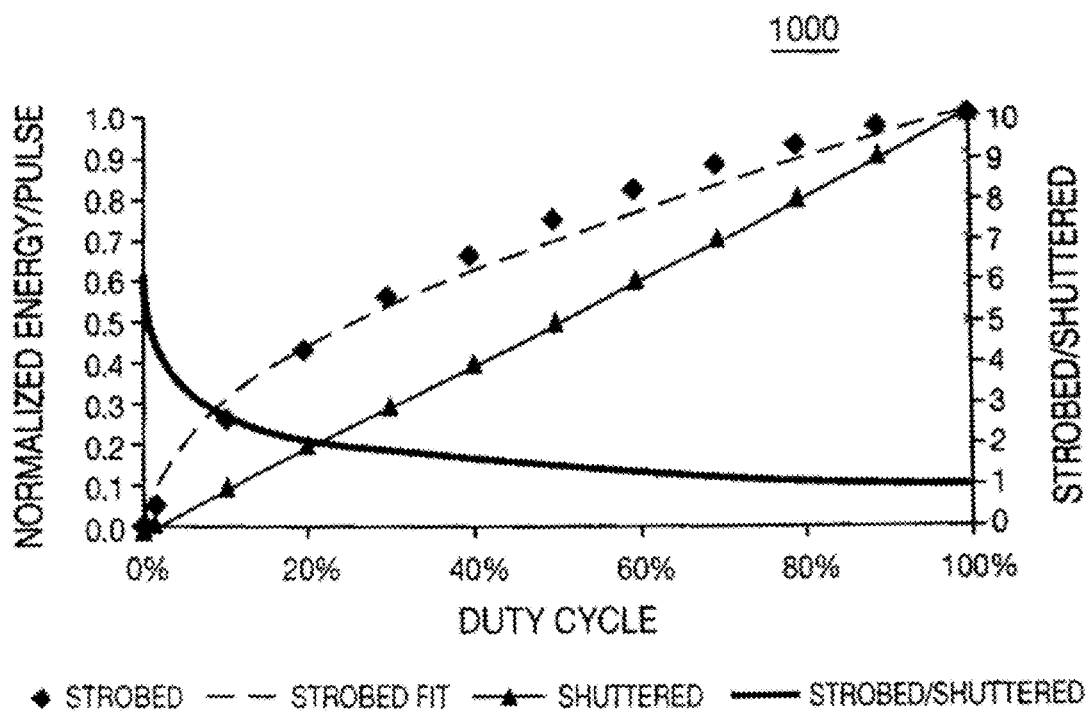
FIG. 6 is a chart showing an analysis of the data from FIG. 5.

FIG. 6 is a chart 1000 showing an analysis of the data from FIG. 5. FIG. 6 shows the results of computing the energy per pulse, normalized to 100% duty cycle for two cases: (1) shuttered illumination with the LED array operating at maximum CW forward current and (2) strobed illumination with the LED array operating at the maximum pulsed forward current. The ratio of strobed to shuttered energy/pulse is always greater than 1. At 10% duty cycle the ratio is approximately 2.5. The details of these results vary depending on the LED specifications, but the general trend is always the same: strobed illumination provides higher maximum energy/pulse than shuttered. In this analysis, it was assumed that the forward voltage drop remained constant as the drive current was varied and that the optical output was proportional to the drive current. The expected deviations from these assumptions are small within the normal operating ranges for LEDs.

In an iris recognition system, a primary health concern is excessive IR irradiation of the human eye. The present invention enables an iris recognition system to customize the IR irradiation of a light source to fit specific environments and avoid potential eye damage. In the near IR, the photons do not have enough energy to represent photo-ionization or photochemical (blue light hazard) hazards, instead, the primary hazard is thermal. The degree of hazard is driven by the amount of energy absorbed per unit area of tissue, the time over which the energy is absorbed, and the area over which the energy is absorbed. Near IR (i.e., 760-1400 nm) eye safety is complicated by the optical elements of the eye. Though the retina is insensitive to near IR, the lens of the eye can still focus near IR illumination. Hence, two different aspects of the illumination should be addressed: radiance (W/m$^2$-sr) of the source and irradiance (W/m$^2$) of the cornea/lens. Irradiance of the lens/cornea determines the thermal effects on the lens/cornea The radiance of the source determines the maximum irradiance of the retina that the eye lens can produce by focusing the source onto the retina. The resulting retinal irradiance then determines the thermal effects at the retina The details of the models used to evaluate the resulting hazards are found in the supplements to the ACGIH TLVs® and BEIs booklets and other safety texts.

To avoid injury to the cornea/lens, the irradiance TLV® for IR radiation (770 nm <λ<3000 nm) of duration greater than 1000 seconds is 10 mW/cm$^2$. For exposures of less than 1000 seconds, the TLV® depends on exposure time as $t^{-3/4}$.

To avoid injury to the retina, the radiance TLV® for IR radiation (770 nm <λ<1400 nm) of duration greater than 10 seconds is 0.6/αR mW/cm2-sr, where R is a retinal thermal hazard function that is wavelength dependent, ranging from 1.0 at 770 nm to 0.02 between 1050 nm and 1400 nm, and α is the angular subtense of the source at the eye. For exposures of less than 10 seconds, the radiance TLV® depends on exposure time as $t^{-1/4}$.

For repetitive exposures such as a light source pulsed at a frequency, f, with a duty cycle, D, for a period of time, T, the TLVs® are more complicated. Exposure to a train of closely spaced pulses of duration, $\tau=D/f$, presents a greater hazard than a single pulse of the same duration. This scenario has not been carefully addressed for non-laser light sources, though both the ACGIH and the IEC have recommendations for the retinal thermal hazard of pulsed laser sources.

Exemplary embodiments of the present invention control IR radiation from a light source to meet all three of the following criteria: single pulse, average, and total on time. The single pulse criterion is that every pulse in the pulse train must be below the TLV® for a pulse of its duration. The average criterion is the average of the pulses in the pulse train must be below the TLV® for a pulse of the duration of the train. The total on time criterion is for a uniform pulse pattern applied for a time, T, sum the total on time of the pulses to form Ttot and compute a TLV® for a pulse of that duration.

These three criteria are reasonable and conservative extrapolations of the single pulse TLVs® for both retinal and corneal/lens TLVs® of non-laser sources. The last of the three can be restated in a form that is easier to understand. If a pulse of length $T_0$ is safe, then breaking up that pulse into a group of shorter pulses dispersed in across a time period $T_1 > T_0$ will also be safe. This criterion is conservative because it is expected that there is some recovers' between pulses.

For both retinal and corneal/lens TLVs®. there is an exposure time beyond which the exposure rate is a constant, i.e., a continuous exposure limit. If the total on time for a pulse train exceeds the continuous exposure limit, 10 seconds for the retinal TLV® or 1000 seconds for the corneal/lens TLV®, there is no relaxation of the TLV®. However, if the total on time for a pulse train is less than those limits, the TLVs® will be relaxed.

In exemplary embodiments of the present invention, shuttering the camera had no effect on the exposure of the eye. Strobing the light source does. If Ttot was less than continuous exposure limit, the TLVs® was relaxed. For retinal effects the TLV® is increased by a factor $D^{-1/4}$ where D is the duty cycle. For corneal/lens effects the TLV® is increased by $D^{-3/4}$. For a 10% duty cycle, the improvements were 1.8 and 5.6 respectively. Output of LEDs of interest was not limited by the radiance of individual LEDs, but rather by the ocular irradiance of an array of LEDs, so the factor 5.6 is relevant. Irradiance is increased by increasing the pulse current to the LEDs (as discussed above) and by adding more LEDs to the array in some embodiments to take advantage of the full factor of 5.6.

Video synchronized, strobed illumination of the present invention gives the system engineer additional system design flexibility. The increase in light level of 5.6 that can be achieved with strobed illumination of duly cycle of 10% can be used to make many different system tradeoffs, resulting in various embodiments. Two tradeoffs are to increase the camera to subject distance or to increase the depth of field. In both cases, the increase is a factor of $\sqrt{5.6}=2.4$. Another option is to increase S/N against background illumination. In this case, the improvement is the product of the increased light level and the inverse of the duty cycle for a factor of 56.

In a first embodiment of the present invention (FIG. 1), a system 100 captures images of an iris of a person or object 102 moving through a volume of space, e.g., a large stand-off distance exists between the subject and the camera/illumination source. In a second embodiment of the present invention (FIG. 3) a subject 102 stands still and peers into the system 300. In both embodiments, it is important to control the illumination of the subject. As such, these systems include synchronized strobe illumination of the iris together with synchronized image capture. By controlling the illumination as described herein, the exposure time is short (i.e., the illumination sensitive object is unharmed) and there is adequate illumination to perform biometric measurement from the resulting images.

While the foregoing is directed to various embodiments of the present invention, other and further embodiments of the invention may be devised without departing from the basic scope thereof. As such, the appropriate scope of the invention is to be determined according to the claims, which follow.

What is claimed is:

1. A computer implemented method for providing strobed image capture, comprising:
    controlling, with an illumination controller, at least one strobed illumination source to limit an amount of radiation from the illumination source that is applied to an iris of a subject;
    synchronizing, with the illumination controller, at least one camera with the strobed illumination source;
    strobing the at least one strobed illumination source with the illumination controller for a series of short pulses over a period of time having an intensity that is greater than a threshold limit value for a continuous wave output of the at least one strobed illumination source over the period of time; and
    capturing at least one image of the iris with the at least one camera, the iris being illuminated at least in part by a plurality of photons from the strobed illumination source.

2. The method of claim 1, wherein the subject having the iris is moving.

3. The method of claim 1, further comprising processing the at least one image to identify the subject.

4. The method of claim 1, further comprising processing the at least one image to provide pupillometry.

5. The method of claim 1 wherein the controlling step further comprises:
    controlling, with the illumination controller, a second illumination source that continuously illuminates iris.

6. The method of claim 1 wherein the at least one image is a video stream.

7. The method of claim 1, wherein the at least one image of the iris is suitable for biometric purposes.

8. The method of claim 7, wherein the biometric purpose is at least one of iris recognition, saccadic motion analysis, and pupillometry.

9. The method of claim 1, wherein a light intensity of the strobed illumination source is increased during a strobe, while an average irradiance of the strobed illumination source remains below a safety threshold.

10. The method of claim 9, wherein a an eye finder provides a plurality of iris images.

11. A system for providing strobed image capture, comprising:
    at least one camera;
    at least one illumination controller for synchronizing with the at least one camera at least one illumination source for illuminating an iris of a subject with a plurality of photons;
    wherein the at least one captures at least one image of the iris at least in part from the plurality of photons reflected from the iris; and wherein the illumination controller is configured to strobe the at least one illumination source for a series of short pulses over a period of time having an intensity that is greater than a threshold limit value for a continuous wave output of the at least one illumination source over the period of time.

12. The system of claim 11, wherein the subject having the iris is moving.

13. The system of claim 11, wherein the at least one image is suitable for biometric purposes.

14. The system of claim 11, wherein a light intensity of the strobed illumination source is increased during a strobe, while an average irradiance of the strobed illumination source remains below a safety threshold.

15. The system of claim 11 further comprising processing the at least one image to identify the subject.

16. The system of claim 11, further comprising processing the at least one image to provide pupillometry.

17. The system of claim 11, wherein the controlling step further comprises:
controlling a second illumination source that continuously illuminates the iris.

18. The system of claim 11, wherein the at least one image is a video stream.

19. The system of claim 13, wherein the biometric purpose is at least one of iris recognition, saccadic motion analysis, and pupillometry.

20. A system for performing iris recognition, comprising:
at least one camera arranged to define an image capture volume and configured to capture a plurality of images of a subject moving through the image capture volume, wherein at least one of the plurality of images contains at least a portion of an iris;
an illumination source;
a controller coupled to the illumination source and the at least one camera, the controller configured to provide illumination of the subject during operation of the at least one camera; and
a processor for processing at least one of the plurality of images containing at least a portion of an iris to perform iris recognition;
wherein the controller is configured to strobe the illumination source; and
wherein a light intensity of the illumination source is increased during a strobe, while an average irradiance of the illumination source remains below a safety threshold.

21. The system of claim 20, further comprising a plurality of cameras arranged to define the image capture volume and configured to capture a plurality of images of the subject moving through the image capture volume.

22. The system of claim 20, wherein the plurality of cameras are configured to capture the plurality of images of the subject substantially simultaneously.

23. The system of claim 20, wherein the controller is configured to strobe the illumination source for a series of short pulses having an intensity that is greater than a threshold limit value for a continuous wave output of the illumination source over the same period of time.

24. The system of claim 20, wherein the controller is configured to strobe the illumination source in synchronization with shuttering of the at least one camera.

25. The system of claim 20, wherein the illumination source creates illumination that does not damage the subject.

26. The system of claim 20, wherein an illumination level provided by the source generates sufucient reflected photons from the subject moving through the image capture volume captured by the at least one camera to produce an iris image suitable for iris biometric analysis when a distance between the at least one camera and the subject is large.

27. The system of claim 26, wherein the for iris biometric analysis is at least one of iris recognition, saccadic motion analysis, and pupillometry.

28. The system of claim 20, wherein at least part of the plurality of images of the subject is provided by the at least one camera in the form of a video stream.

29. The system of claim 20, wherein the image capture volume is greater than about 22.5 cm$^3$.

30. The system of claim 20, wherein the plurality of images of the subject are captured by the at least one camera without stopping the subject.

31. The system of claim 20, wherein the image capture volume is configured to allow movement of the subject.

* * * * *